US00PP21459P2

(12) United States Plant Patent

Bathaeian

(10) Patent No.: US PP21,459 P2

(45) Date of Patent: Nov. 9, 2010

(54) **VARIETY OF *VERBENA* PLANT NAMED 'GRUELOX 02'**

(50) Latin Name: *Verbena hybrida*
Varietal Denomination: Gruelox 02

(75) Inventor: Mehdi Bathaeian, Waltrop (DE)

(73) Assignee: Grünewald Veredelings B.V., 's Gravenzande (NL)

( * ) Notice: Subject to any disclaimer, the term of this patent is extended or adjusted under 35 U.S.C. 154(b) by 0 days.

(21) Appl. No.: 12/387,214

(22) Filed: Apr. 29, 2009

(51) Int. Cl.
*A01H 5/00* (2006.01)

(52) U.S. Cl. ..... Plt./308

(58) Field of Classification Search ..... Plt./308
See application file for complete search history.

(56) References Cited

OTHER PUBLICATIONS

GTITM UPOVROM Citation for 'Grulox 02' as per QZ PBR 20081456; July 26, 2008.*

* cited by examiner

*Primary Examiner*—Kent L Bell
(74) *Attorney, Agent, or Firm*—The Webb Law Firm

(57) ABSTRACT

A new and distinct *Verbena* plant named 'Gruelox 02' having plentiful and large flowers with a small purple eye in the middle.

1 Drawing Sheet

Botanical classification: *Verbena hybrida.*
Varietal denomination: 'Gruelox 02'.

BACKGROUND OF THE INVENTION

The present invention comprises a new and distinct cultivar of *Verbena* plant known by the varietal name 'Gruelox 02'. The new variety was discovered in August of 2003 in a selected breeding program in Waltrop, Germany. The purpose of the breeding program was to produce a new variety of Verbena with large flowers and improved mildew resistance. The new variety was selected from a cross of proprietary unpatented breeding plants identified as 5-11-1 (female parent, unpatented) and 4-3 (male parent, unpatented). The new variety exhibits a bushy, compact growth habit that is similar to its parents, but exhibits more and larger flowers than both parents and also exhibits hard and glossy leaves. Further, 'Gruelox 02' has larger flowers (20 mm vs. 8-10 mm) than *Verbena* plant 'Sumverdi'. The new variety was first asexually reproduced in October 2003 by tipcuttings in Waltrop, Germany. The new variety has been trial and field tested and has been found to retain its distinctive characteristics and remain true to type through successive asexual propagations.

The following traits also distinguish 'Gruelox 02' as a new and distinct cultivar from other *Verbena* varieties known to the breeder:

1. 'Gruelox 02' exhibits a small, purple eye;
2. 'Gruelox 02' has plentiful flowers per spike; and
3. 'Gruelox 02' has large flowers.

DESCRIPTION OF THE DRAWINGS

The accompanying photographic drawing illustrates the new variety, with the color being as nearly true as is possible with color illustrations of this type.

DESCRIPTION OF THE PLANT

Figure 1:
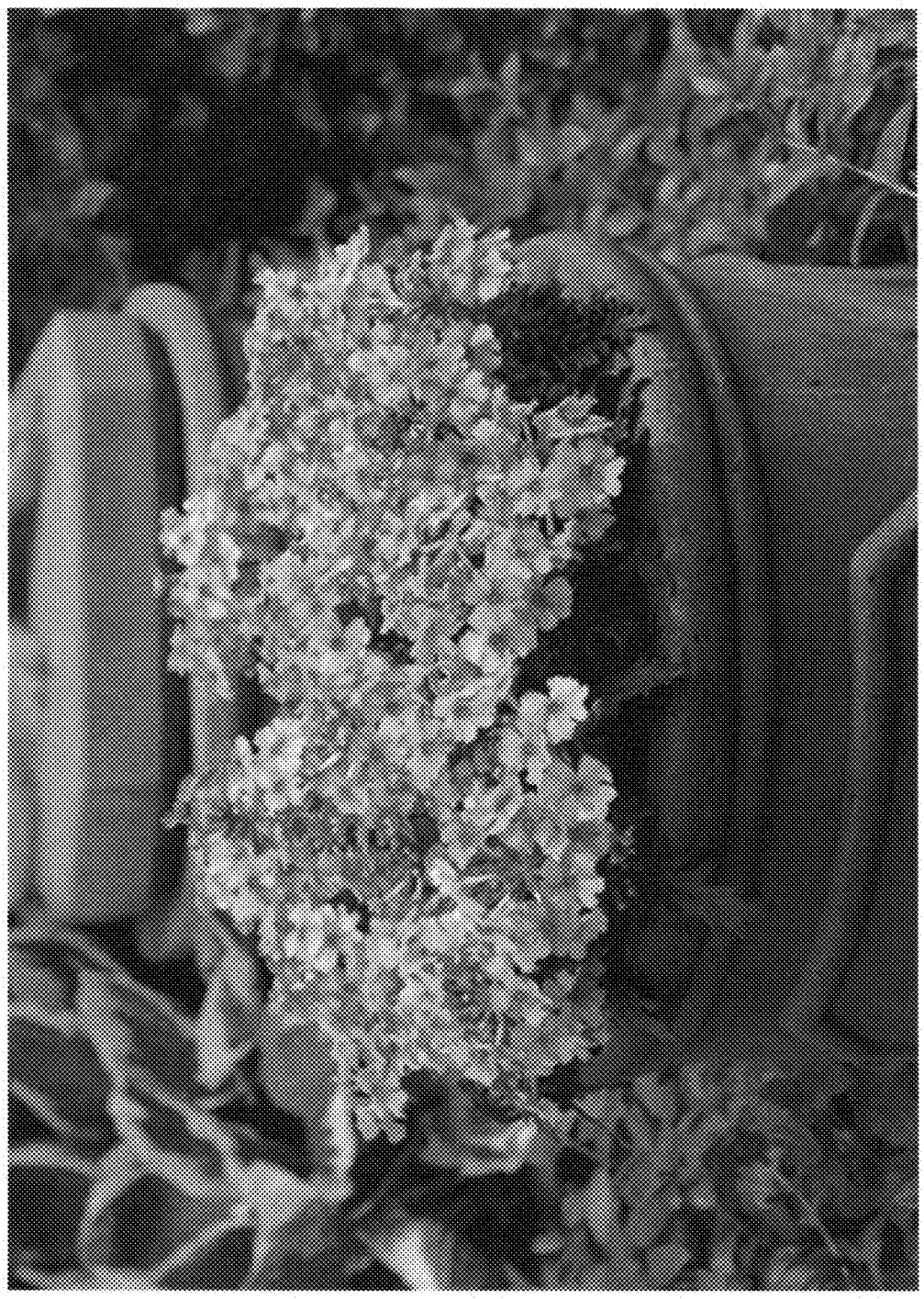
FIG. 1 is a photograph of the plant.

The following detailed description sets forth characteristics of the new cultivar. The data which defines these characteristics were collected by asexual reproductions by cuttings carried out in Waltrop, Germany. Plants for the description were 11 weeks old, grown in a greenhouse during the Summer in 10.5 cm containers. The color readings were taken in an office under artificial light. Color references are primarily to The 2001 R.H.S. Colour Chart of The Royal Horticultural Society of London.

PLANT

Height (from soil to top of flowers): Approximately 20 cm.
Diameter: Approximately 20 cm.
Vigor: Compact.
Roots:
- *Habit.*—Spreading.
- *Time to initiate roots.*—About 10 days at 18° C.
- *Time to develop roots.*—About 21 days at 18° C.

Time to finish a flowered plant: About 10-12 weeks in a 10.5 cm container.
Branching habit: Bushy.
Lateral branches:
- *Color.*—146B.
- *Texture.*—Smooth.
- *Diameter.*—Approximately 3-4 mm.
- *Internode length.*—Approximately 20-25 mm.

Foliage:
- *Arrangement.*—Opposite.
- *Size of leaf.*—Length: 25-30 mm. Width: Approximately 18-20 mm.
- *Shape of leaf.*—Lanceolate.
- *Shape of apex.*—Acute.
- *Shape of base.*—Obtuse.
- *Texture.*—Smooth.
- *Margin.*—Crenate.

*Color.*—Young leaves: Upper surface: 137A. Lower surface: 137D. Mature leaves: Upper surface: 137A. Lower surface: 137B.
*Petiole.*—Length: 5 mm. Diameter: 1 mm. Color: 138B.
*Veins.*—Venation type: Pinnate. Color: Upper surface: 138B. Lower surface: 138B.

FLOWER

Natural flowering season: From April until October.
Bud (described before opening):
*Shape.*—Long; 5 parted.
*Diameter.*—3 mm.
*Length.*—10-11 mm.
*Color.*—N57C.
Spike:
*Number of flowers per spike.*—Approximately 35-45.
*Diameter.*—Approximately 15-18 mm.
*Length.*—Approximately 8-10 cm after flowering.
*Color.*—68A.
Inflorescence:
*Type.*—Round umbel.
*Length.*—35-40 mm.
*Diameter.*—50-58 mm.
*Number of flowers per inflorescence.*—Fully opened: 9-10. Half opened: 2-3. Buds: 2-3.
Pedicel:
*Umbel length.*—35-45 mm.
*Diameter.*—1.8 mm.
*Color.*—Almost 137C.
Corolla:
*Form.*—Fused petals.
*Petals/lobes.*—Number: 5. Length: Approximately 7-9 mm. Width: Approximately 6-7 mm. Shape: Obovate. Aspect: Flat. Margin: Lobated. Apex: Heart-shaped. Texture and appearance: Smooth. Color: When opening: Upper surface: N57 with a 71B eye. Lower surface: N57. Fully opened: Upper surface: N57 with a 71B eye. Lower surface: N57.
*Throat.*—Color: 130D. Texture: Smooth.
*Tube color.*—130D.
*Tube length.*—21 mm.
Calyx:
*Form.*—Fused at base; cylindrical.
*Length.*—Approximately 8-11 mm.
*Diameter.*—2 mm.
*Sepal.*—Shape: Cylindrical; 5 connected sepals. Margin: Acuminate. Texture: Smooth. Color: Upper surface: 137B. Lower surface: 137B to 137D.
Disease resistance: No resistance or susceptibility to pests or diseases noted to date.
Fragrance: None.
Temperature tolerance: From 1° C. to 45° C.
Lasting quality: Good.

REPRODUCTIVE ORGANS

Stamens:
*Number.*—4.
*Filament length.*—0.5 mm.
*Anthers.*—Shape: Oval. Length: 0.01 mm. Color: N144D.
*Pollen.*—Color: 154C. Amount: Minimal.
Pistil:
*Length.*—10-12 mm.
*Style.*—Length: Less than 0.5 mm. Color: 137B to 137D.
*Stigma.*—Shape: Oval. Color: 137D.
Seed production: None.

I claim:

1. A new and distinct variety of *Verbena* plant named 'Gruelox 02' substantially as shown and described herein.

* * * * *